(12) United States Patent
Marian

(10) Patent No.: US 6,969,354 B1
(45) Date of Patent: Nov. 29, 2005

(54) ADAPTABLE INTRAOPERATIVE OR ENDOCAVITY ULTRASOUND PROBE

(75) Inventor: Vaughn R. Marian, Saritoga, CA (US)

(73) Assignee: Acuson Corporation, Mountain View, CA (US)

( * ) Notice: Subject to any disclaimer, the term of this patent is extended or adjusted under 35 U.S.C. 154(b) by 413 days.

(21) Appl. No.: 09/964,229

(22) Filed: Sep. 25, 2001

(51) Int. Cl.⁷ .............................................. A61B 8/14
(52) U.S. Cl. ...................... 600/459; 600/437; 600/439; 600/462; 600/466; 600/467
(58) Field of Search ................. 600/459, 437, 600/439, 462, 463, 466, 467; 128/899

(56) References Cited

U.S. PATENT DOCUMENTS

| | | | |
|---|---|---|---|
| 5,163,421 A | * 11/1992 | Bernstein et al. | 606/128 |
| 5,235,964 A | * 8/1993 | Abenaim | 600/139 |
| 5,469,852 A | * 11/1995 | Nakamura et al. | 600/463 |
| 5,469,853 A | * 11/1995 | Law et al. | 600/463 |
| 5,471,988 A | * 12/1995 | Fujio et al. | 600/439 |
| 5,485,842 A | * 1/1996 | Quistgaard | 128/916 |
| 5,488,955 A | * 2/1996 | Dias | 600/459 |
| 5,503,115 A | * 4/1996 | Franzke et al. | 122/390 |
| 5,503,155 A | * 4/1996 | Salmon et al. | 600/463 |
| 5,681,263 A | * 10/1997 | Flesch | 600/141 |
| 5,833,695 A | * 11/1998 | Yoon | 606/128 |
| 5,845,646 A | * 12/1998 | Lemelson | 128/899 |
| 5,865,650 A | 2/1999 | Marian, Jr. et al. | |
| 5,897,503 A | 4/1999 | Lyon et al. | |
| 5,916,169 A | 6/1999 | Hanafy et al. | |
| 5,923,115 A | 7/1999 | Mohr, III et al. | |
| 5,938,616 A | 8/1999 | Eaton et al. | |
| 5,957,850 A | 9/1999 | Marian, Jr. et al. | |
| 5,964,709 A | * 10/1999 | Chiang et al. | 600/447 |
| 6,036,645 A | * 3/2000 | Drost et al. | 600/463 |
| 6,083,170 A | * 7/2000 | Ben-Haim | 600/463 |
| 6,164,277 A | * 12/2000 | Merideth | 606/139 |

* cited by examiner

*Primary Examiner*—Eleni Mantis-Mercader
*Assistant Examiner*—William C. Jung

(57) ABSTRACT

An intraoperative or endocavity ultrasound probe for insertion into a patient is provided. An adaptable or adjustable section is provided between the handle and the transducer for rotating the transducer relative to the handle prior to insertion within the patient. The adjustable or adaptable section maintains the adjusted or rotated position while the probe is in use within the patient. The adjustable or adaptable section stays in the same pre-bent position, such as by using a memory-less device or material, and is free of user adjustment while the probe is in use.

27 Claims, 3 Drawing Sheets

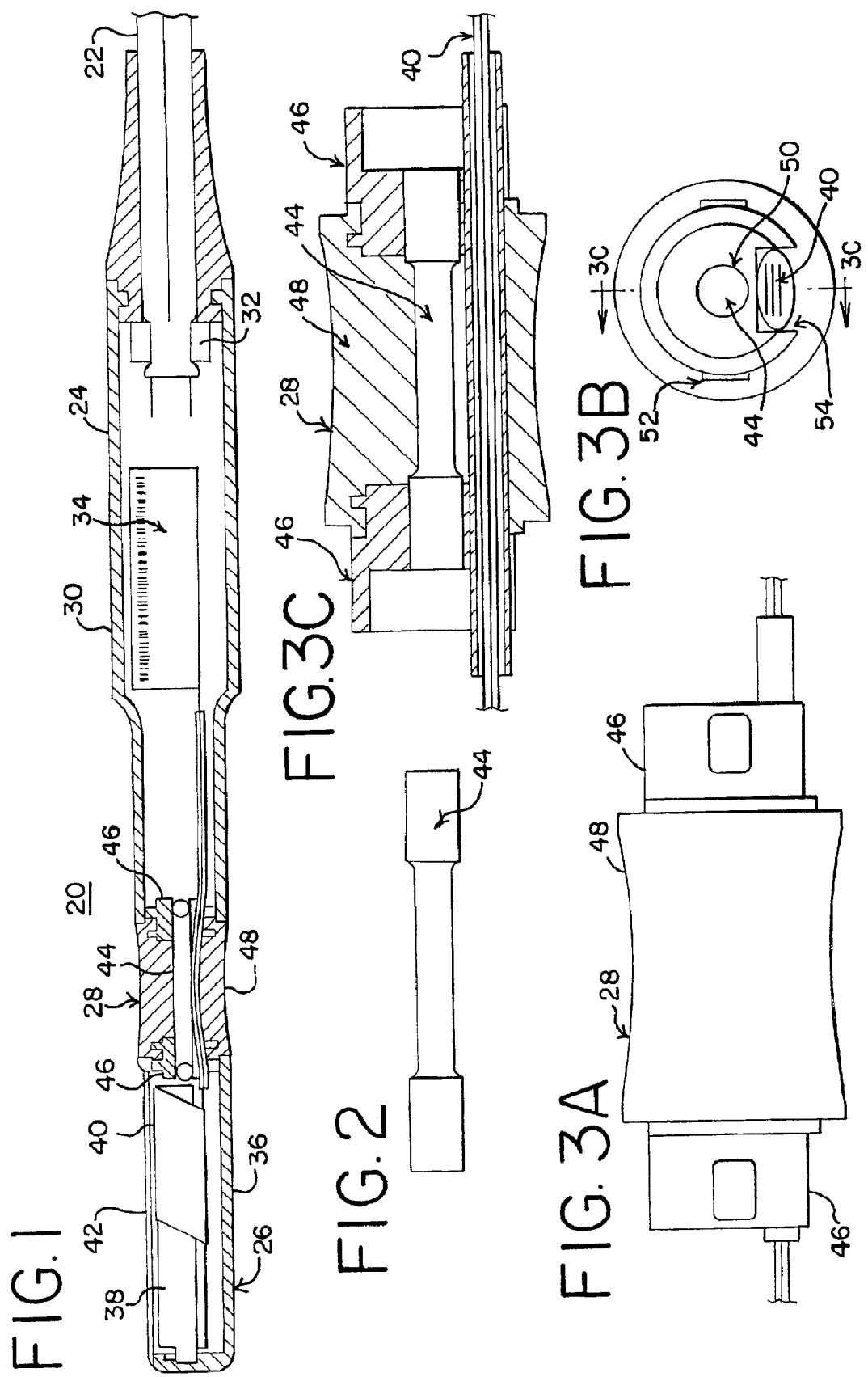

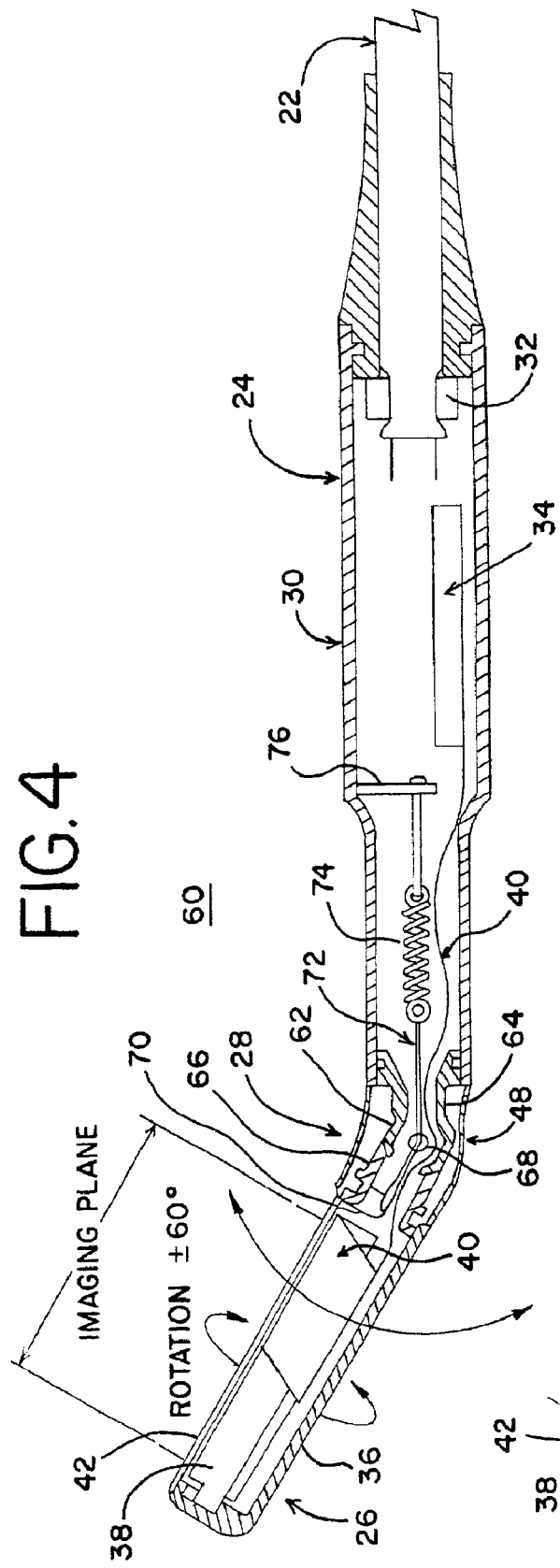

ADAPTABLE INTRAOPERATIVE OR ENDOCAVITY ULTRASOUND PROBE

BACKGROUND

This invention relates to ultrasound probes. In particular, versatile intraoperative and endocavity ultrasound probes are provided.

Intraoperative ultrasound probes are used during surgical procedures for imaging within a patient. For example, an intraoperative probe is inserted through an incision on a patient's abdomen. A transducer portion is placed adjacent to the patient's liver, and the liver is imaged.

Intraoperative probes are rigid. The imaging plane of the probe is oriented by rotating the handle. Different intraoperative probes are provided for different surgical procedures. One shape may not adequately address the needs for different surgical procedures, so a multitude of intraoperative ultrasound probes with different shapes are often required.

Typical endocavity ultrasound probes are shaped for insertion into a natural orifice of a patient; these devices include esophageal, vaginal or rectal probes. Typically, vaginal or rectal probes are rigid or semi-rigid. Esophageal probes usually have a transducer mounted on the end of a flexible section. Controls in the handle allow the operator to adjust the spatial orientation of the transducer with respect to the organ of interest during the diagnostic procedure.

BRIEF SUMMARY

The present invention is defined by the following claims, and nothing in this section should be taken as a limitation on those claims. By way of introduction, the preferred embodiments described below include an intraoperative or endocavity ultrasound probe for insertion into a patient. An adaptable or adjustable section is provided between the handle and the transducer for rotating the transducer relative to the handle prior to insertion within the patient. The spatial orientation of the transducer with respect to the handle does not change during the diagnostic or surgical procedure. Different views of the anatomy may be acquired by adjusting the handle orientation.

In a first aspect, an intraoperative ultrasound probe for insertion into a patient is provided. The intraoperative ultrasound probe has a handle section and a transducer section. The transducer section includes an ultrasound transducer. An improvement of the intraoperative ultrasound probe is provided by adding an adaptable section between the handle section and the transducer section.

In a second aspect, an intraoperative or endocavity ultrasound probe for insertion into the cavity of a patient is provided. The probe includes a transducer housing and a handle housing. An adjustable section joins the transducer housing to the handle housing. The adjustable section has a flexible covering and a device to maintain an adjusted position without steering or control wires.

In a third aspect, a method for using an intraoperative or endocavity ultrasound probe is provided. Prior to inserting the probe into a cavity of a patient, a first axis of the transducer housing is rotated relative to a second axis of a handle housing. The relative position of the first and second axes are maintained during insertion of the probe into the cavity of the patient.

Further aspects and advantages of the invention are discussed below in conjunction with the preferred embodiments.

BRIEF DESCRIPTION OF SEVERAL VIEWS OF THE DRAWINGS

The components in the figures are not necessarily to scale, emphasis instead being placed upon illustrating the principles of the invention. Moreover, in the figures, like reference numerals designate corresponding parts throughout the different views.

FIG. 1 is a cross-sectional view of an endocavity ultrasound probe of one embodiment.

FIG. 2 is a top view of a flexible link of one embodiment for use in the intraoperative probe of FIG. 1.

FIGS. 3A–C are side views, end views and cross-sectional view, respectively, of one embodiment of a adaptable section for use in the intraoperative probe of FIG. 1.

FIG. 4 is a cross-sectional diagram of another embodiment of a intraoperative ultrasound probe.

FIGS. 5A and 5B are across-sectional diagrams of yet another embodiment of an intraoperative ultrasound probe.

DETAILED DESCRIPTION OF THE PREFERRED EMBODIMENTS

Figure 5B:
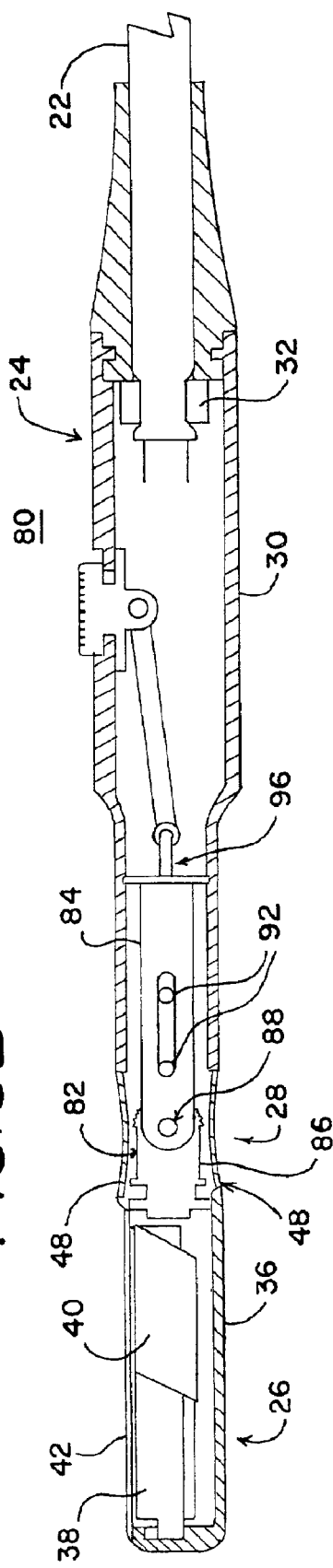

By pre-bending an endocavity or intraoperative ultrasound probe, a surgeon is able to optimize the shape of the probe for more effective use during subsequent surgery or other procedures. The adaptable probe is adjusted so the transducer is rotated at an angle to the handle. The bend is maintained so the probe can be inserted to a patient without further control needed by the surgeon or other user.

Pre-bending allows the endocavity or intraoperative probe to be optimized for a particular type of imaging or procedure. For example, little or no rotation or greater amounts of rotation may be provided for any of imaging the liver, other organ, aorta, or other vessels during surgery through a small or large surgical incision in the abdomen. An adaptable section of the probe allows the transducer to be manipulated into any imaging angle and strategically placed for better diagnostic imaging during an operation, such as allowing imaging behind an organ. Better imaging may allow an operation to proceed with minimal invasiveness. The same probe can be used for different types of surgeries and for imaging different portions of the body by adjusting the adaptable section.

FIG. 1 shows one embodiment of an intraoperative ultrasound probe operable to be pre-bent or pre-formed for insertion into a patient. The ultrasound probe 20 includes a cable 22, a handle section 24, a transducer section 26 and an adaptable or adjustable section 28. Additional, different or fewer components may be used.

The cable 22 comprises one or more conductors covered with a flexible outer jacket or cover. The cable communicates bidirectional electrical signals between the probe 20 and the ultrasound imaging system. In one embodiment, the cable 22 comprises a plurality of coaxial conductors covered by an elastomeric cover or jacket. The handle section 24 comprises a handle housing 30, a cable clamp 32 and a flexible circuit termination 34. Additional or different components can be provided. The handle housing 30 comprises plastic, silicone, other polymer or other material. The handle housing 30 is formed for grasping or gripping by a person, such as including ridges associated with fingers or other gripping materials. The handle housing 30 has a square, rectangular, circular, oblong or other cross-sectional shape. The handle housing 30 extends along a handle axis from the cable 22 to the adaptable section 28. The length of the handle housing 30 along the handle axis is associated with intended use. In one embodiment, the handle housing 30 comprises about 4 inches along the handle axis, but other lengths may be used.

The cable clamp 32 consists of two parts connected together by a hinge and screw or by multiple screws or multiple latches. The clamp 32 compresses the cable 22 and is designed to mechanically fix the cable to the interior of the handle 30 or to fix the cable to the strain relief which is in turn fixed to the handle 30. The individual coaxial conductors of the cable 22 connect with the flexible circuit termination 34.

The transducer section 26 includes a transducer housing 36, a transducer 38, and a flex circuit 40. The transducer housing 26 comprises plastic, polymer, silicone or other material for insertion within a patient. In one embodiment, the transducer housing 36 comprises material that may be sterilized for reusing the ultrasound probe 20. The transducer housing 36 is shaped to allow insertion within the patient and navigation within the patient. In one embodiment, the transducer housing 36 is smooth and sized as small as possible while providing space for the transducer 38.

The transducer housing 36 also includes a window or aperture 42 for transmitting or receiving acoustic energy. In one embodiment, the window 42 comprises the same material as the rest of the transducer housing 36. In alternative embodiments, a different material for providing acoustic matching between the transducer 38 and a patient and/or for focusing acoustic energy is provided.

The transducer array 38 comprises an array of piezoelectric or capacitive membrane transducer elements capable of both transmitting ultrasound energy into the body and detecting reflecting ultrasound energy from internal organs. The reflected energy is used by the ultrasound imaging system to construct a diagnostically useful image of the internal organs. One dimensional, two dimensional, 1.5 dimensional, circular, linear, curved, or other arrays may be used. For example, a linear one-dimensional array extends along most of the length of the transducer housing 36 from the adaptable section 28 to the distal end of the probe (i.e. along the transducer housing axis). In alternative embodiments, the transducer array 38 extends along a smaller portion of the transducer housing 36. In yet other alternative embodiments, the transducer array 38 is positioned at the distal end or around the circumference of the transducer housing 36.

The flex circuit 40 provides an electrical interconnection between the transducer array 38 and the coaxial conductors. The flex circuit 40 extends through the flexible section 28 to the flex circuit termination 34. A conduit, such as a thin elastomer, may be provided for housing the flex circuit 40 through the adaptable section 28. The flex circuit 40 provides signals to and receives signals from the cable 22 and the transducer 38.

The adaptable or adjustable section 28 comprises a link 44, two link mounts 46 and a flexible covering 48. The flex circuit 40 also passes through the adaptable or flexible section 28. The adaptable section 28 is molded from thermoplastic rubber or another elastomeric material as a pre-assembly or molded after connecting the link 44 with the transducer and handle sections 24, 26. Additional or fewer components may be provided, such as molding the link mounts 46 into either or both of the handle housing 30 or transducer housing 36.

The link 44 comprises a metal shaft, but other materials may be used. For example, the link 44 comprises an aluminum wire, such as pure aluminum (e.g., 2S or 100 aluminum). The link 44 comprises a bendable, non work-hardening ductile (i.e., memory-less) material. Once the link 44 is bent, the link 44 maintains the bend so that any one of a plurality of different positions of the link 44 may be maintained. By bending the link 44, the axis of the transducer section 26 or the transducer housing 36 is positioned at an angle relative to the axis of the handle section 24 or handle housing 30. Since the link 44 maintains the angle or position after bending, the probe 20 may be used without steering or control wires or other user control while a portion of the probe 20 is inserted within a cavity of the patient, such through a natural orifice or through a surgical incision. The link 44 allows the probe 20 to be pre-bent or pre-formed for each use.

FIG. 2 shows one alternative embodiment of the link 44 formed from a ductile aluminum wire. The link 44 has enlarged ends for mounting the ends of the link in the link mounts 46. In alternative embodiments, the link 44 comprises a straight metal shaft or wire, and the link mounts 46 hold the link 44 by compression. In yet other alternative embodiments, the link 44 includes apertures, splines, or shaped ends for mounting to the link mounts 46.

In one embodiment, the malleability of the link 44 is a function of an external force. For example, the link 44 comprises an alloy or other material more malleable in response to an external force than absent the external force. Application of heat, microwaves, ultrasound energy, electric energy, other electromagnetic forces or other energy increases the malleability of the link 44 for adjusting or bending prior to use within a patient. During use of the ultrasound probe 20 within the patient, the link 44 is less malleable and less likely to bend. For example, a microwave sleeve is provided to focusing energy on the link 44. Microwaves are applied to make the link 44 more malleable. The adjustable section 28 is positioned or bent as desired after the microwave sleeve is removed. The ultrasound probe 20 is allowed to rest or cool before use. During use, a greater force is required to bend the link 44 than was required immediately after applying microwaves. As another example, the link 44 comprises the entire adaptable section 28, such as a framework or solid structure of ductile material without a protective sleeve or covering. Heat is applied, such as with a torch or burner, to make the adaptable section 28 more malleable.

In yet another embodiment, the link 44 is a titanium nickel alloy or other shaped memory alloy (e.g. Nitinol). Application of heat (e.g. from −100 degrees Celsius to 100 degrees Celsius as a function of the alloy) causes the link 44 to regain an original shape. If the shape is then bent and distorted during use, the original shape is obtained by applying heat. In the low temperature state (i.e. martensite), the yield strength may be between 10,000 and 20,000 psi. In the high temperature state (i.e. austenite), the yield strength may be between 30,000 and 100,000 psi. Accordingly, the link 44 is bent or adapted in the low temperature state for use, but may regain a starting, optimal or original shape for use by heating. Thus, the link 44 is pre-bent to the correct shape for the surgical or diagnostic procedure. After the procedure, it would be restored to its "normal" shape by applying heat using one of several methods described above.

FIGS. 3A, 3B and 3C show side, front and cross-section views of the link mounts 46 and adaptable section 28 using the link 44 of FIG. 2. The link mounts 46 comprise metal or plastic attached to the transducer housing or the handle housing by epoxy or adhesive. The link mount 46 includes an aperture 50 keyed or otherwise shaped for holding the link 44. A grooved or raised key 52 is also provided for mounting or connecting with either the handle housing 30 or the transducer housing 36. The shape and size of the link mount 46 corresponds to a size and shape of the inner diameter of the handle housing 30 or the transducer housing 36. The link mount 46 mounts to the handle housing 30 or transducer housing 36 using adhesives, pressure, latching mechanisms or other methods. The link mount 46 also includes a groove or aperture 54 for passing the flex circuit 40 or other cabling from the transducer section 26 to the cable 22.

In the embodiment of FIG. 1, the link 44 comprises ductile wire or shaft with curved or bent ends. The curved or bent ends of the link 44 are staked to the link mounts 46, such as providing one or more pressure points for holding the link 44. For example, a portion of the link mount 46 is inserted and bonded to the remainder of the link mount 46 after the link 44 is positioned. The portion is pressed against the end of the link 44. Bonding or adhesion of the link 44 to the link mounts 46 may alternatively or additionally be used.

FIG. 1 also shows the flexible covering 48 on the adaptable or adjustable section 28. The flexible covering 48 comprises a polymer or other flexible material. For example, the flexible covering 48 comprises a silicone based elastomer or other materials that can be sterilized or otherwise inserted into a patient. A generally solid block of rubber or other material is formed as the flexible covering 48 by room temperature vulcanization or other processes. In alternative embodiments (see FIGS. 4 and 5A and B) the flexible covering 48 may be formed as an accordion, generally spring-shaped or smooth structure for allowing additional flexibility.

FIG. 4 shows an intraoperative ultrasound probe 60 with an alternative embodiment of the adaptable or adjustable section 28. The rotated, bent or adjusted position of the transducer section 26 relative to the handle section 24 is maintained by friction in a ball joint 62. The ball joint 62 includes two link mounts 64 and 66. One link mount 64 includes a spherical section, cylindrical section, semi-circular section or ball. The link mount 64 comprises metal, plastic, polymer or other material. In one embodiment, lubricating oil, grease, grit, gripping or other material is placed on or embedded within the link mount 64. The link mount 64 is also formed for adhesion to the handle housing 30. An aperture passes through the link mount 64. The link mount 64 also includes a pin 68 formed, glued, mounted or positioned within the link mount. The pin 68 comprises the same or different material as the link mount 64.

The other link mount 66 comprises metal, plastic, polymer or other material. In one embodiment, one link mount 64 comprises metal and the other link mount 66 comprises plastic or vice versa. In alternative embodiments, the link mounts 64 and 66 comprise a same material. The other link mount 66 is adapted to slide over the spherical or rounded portion of the link mount 64 for rotation of the transducer section 26 relative to the handle section 24. In alternative embodiments, one or both of the mount links 64 and 66 include grooves or ridges for pre-determined positions of the transducer section 26 relative to the handle section 24. The other link mount 66 is also adapted for latching, adhering or mounting to the transducer housing 36. The link mount 66 also includes an aperture allowing the flex circuit 40 or other cabling to pass through the ball joint 62.

The link joint 66 also includes a mounting plate 70 with an aperture for connection to a tensioned wire 72. In alternative embodiments, the mounting plate 70 comprises a hook, adhesive pad or other mechanism for connecting the tensioned wire 72 to the transducer section 26. In yet other alternative embodiments, the mounting plate 70 or other mechanism connects to the transducer housing 36. The mounting plate 70 is positioned such that the tensioned wire 72 connects at a generally center position along the diameter or circumference of the transducer housing 36.

The tensioned wire 72 comprises metal, plastic, nylon, or other material. The tensioned wire 72 connects from the mounting plate 70 to a spring 74. The tensioned wire 72 extends adjacent to or through the pin 68. Where the transducer section 26 is to be rotated in only one direction, such as from 0° to +30°, the tensioned wire 72 is positioned below the pin 68. For rotation up or down such as ±30°, the tensioned wire 72 is positioned through the pin 68 or through an aperture on the pin 68. The pin 68 acts to transfer the force on a tensioned wire 72 from the handle section 24 to the transducer section 26. By maintaining the tensioned wire 72 at the center of the ball joint 62, the force is equally transferred, avoiding a tendency to reposition without user-applied force. The tension on the wire 72 maintains the position of the transducer section 26 relative to the handle section 24 by friction on the ball joint 62 between the two mount links 64 and 66.

The spring 74 comprises a metal (e.g., stainless steel), plastic or other spring for tensioning the tensioned wire 72. In alternative embodiments, air or fluid pressure is used to tension the wire 72. The spring 74 connects with a spring mounting plate 76. The spring mounting plate 76 connects the spring 74 to the handle housing 30 or link mount 64. In alternative embodiments, the spring 74 includes an extension or connects directly to the housing 30. The spring mounting plate 76 maintains the spring 74 at the center of the diameter or circumference of the handle housing 30, but may position the spring 74 at other locations. The spring provides the normal force for friction to hold the position of the handle section 24 relative to the transducer section 26.

The adaptable section 28 includes a covering 48 as discussed above. In one embodiment, the covering 48 is a flexible smooth rubber or plastic material, such as a silicone based elastomer, that allows rotation of the transducer section 26 by 45° relative to the handle section 24 and prevents build-up of material in pockets or accordioned sections.

FIGS. 5A and 5B show an intraoperative ultrasound probe 80 with yet another alternative adaptable or adjustable section 28. The adaptable section 28 includes the flexible covering 48 as discussed above and a latch device 82.

The latch device 82 includes two link mounts 84 and 86. The link mounts 84 and 86 comprise metal, plastic or other material adapted for mounting or connection with the handle housing 30 and the transducer housing 36. The link mounts 84 and 86 connect together by an axle 88. The link mount 84 connected with the handle housing 30 includes a slide aperture 90. In alternative embodiments, a groove is provided. Pins 92 are positioned within the slide aperture 90.

Figure 6:
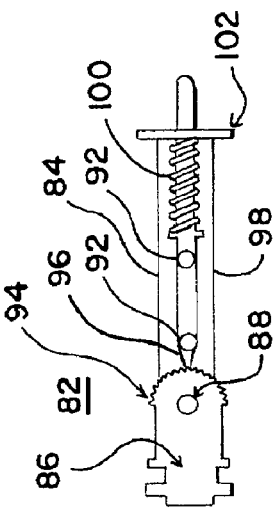
FIG. 6 is a cross-sectional diagram of a latch mechanism of one embodiment for use in the intraoperative ultrasound probe of FIGS. 5a and b.

FIG. 6 is a cutaway of the latch 82. The latch 82 includes a notch portion or locking wheel 94 on one of the mounting links 86. The axle 88 is centered relative to the notch portion 94. The notches on the notch portion 94 rotate along a circular circumference relative to the axle 88 to maintain a substantially same radius from the axle 88 to the various notches on the notch portion 94. The axle 88 rotatably connects the mounting link 86 to the mounting link 84. The notched portion 94 releasably connects with a locking pawl 96.

The locking pawl 96 comprises a metal, plastic or other material with a pointed end or shaped end for mating with one or more notches on the notch portion 94. The locking pawl 96 also includes one or more pins 92 for slidably engaging one or two plates 98. For example, the pins 92 extend from two sides of the locking pawl 96 into two plates 98 on opposite sides of the locking pawl 96. A spring 100 biases the locking pawl 96 against the notch portion 94. The spring 100 comprises stainless steel or other material and rests against a mounting plate 102. The locking pawl 96 extends through the mounting plate 102.

For rotating the transducer section 26 relative to the handle section 24, the locking pawl 96 is forced away from the notch portion 94. The notch portion 94 is rotated about the axle 88 in response to force on either of the handle or transducer sections 24, 26. The spring 100 is then allowed to bias the locking pawl 96 against a notch for maintaining the latch 82 and the adaptable section 28 at a selected angle of rotation.

FIGS. 5A and 5B show one embodiment for applying force to the locking pawl 96. A link 104 connects the locking pawl 96 to a thumb or finger slide 106. The link 104 and slide 106 comprise plastic, metal or other material. The slide 106 is positioned in an aperture of the handle housing 30. The aperture allows the slide 106 to move between two positions associated with a locked position and a released position of the locking pawl 96. The spring 100 biases the slide 106 into the locked position. In one embodiment, the slide 106 includes ridges, gripping material or texture for providing friction to a user's thumb or fingers.

Figure 7:
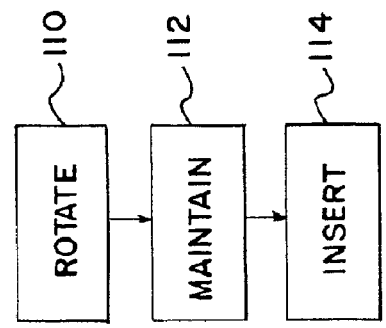
FIG. 7 is a flow chart diagram of one embodiment of use of an intraoperative or endocavity ultrasound probe with an adaptable or adjustable section.

FIG. 7 shows a flow chart diagram representing use of any of the intraoperative probes 20, 60, 80 shown in FIGS. 1, 4, 5a and 5b. In act 10, the transducer section 26 is rotated relative to the handle section 24 as shown in FIGS. 5A and 5B. One of multiple possible positions may be selected. In one embodiment, a range of rotation of ±30° is provided. In other embodiments, ±45° or 60° may be provided, but any of various pitch angles may be used. In one embodiment, a larger angle of rotation is provided in one direction than another, such as providing no rotation in one direction along the pitch angle and 30 or more degrees of rotation in the other pitch direction. The plurality of positions associated with the rotation is determined as a function of the type of adaptable section. For example, the notches of the notch portion 94 of the latch 82 determine the various selectable positions. As yet another example, the embodiments of FIG. 1 and FIG. 4 allow for bending the metal link 44 or adjusting the ball joint 62 to various positions. The metal link 44 and the ball joint 62 may allow for rotation of the transducer section 26 relative to the handle section 24 in a yaw angle, providing both pitch and yaw rotation.

Rotation is provided in response to user-applied force. For example, the user desires to adjust the imaging plane associated with the transducer section 26 relative to the handle section 24 for intraoperative imaging of an organ or vessel. The user grasps the handle section 24 with one hand and the transducer section 26 with another hand, and applies a bending force. For the embodiment shown in FIGS. 5A and 5B, the user also moves the slide 106 so that the locking pawl 96 disengages from the notch portion 94 to allow rotation. The user may reposition or re-adjust the adaptable section 28 until a desired angle of rotation in pitch and/or yaw of the transducer section 26 to the handle section 24 is provided. As a surgical procedure warrants or for different surgical procedures, the surgeon repositions or re-adjusts the angle of rotation. The same intraoperative probe 20, 60, 80 may be used for various procedures or within a single procedure but repositioned at different angles of rotation.

After rotating in act 110, the angle of rotation is maintained in act 112. The metal link 44, the ball joint 62 or the latch 82 maintains the selected angle of rotation. Since the adaptable section 28 is memory-less, the transducer section 26 does not rotate to a neutral position relative to the handle section 24. Accordingly, a surgeon can pre-bend or select an angle of rotation for use during subsequent surgical procedure. The angle of rotation is set before inserting the intraoperative probe into a patient's body cavity, such as through a surgical incision, and is set free of guide wires or other devices for adjusting during use.

In act 114, the surgeon inserts the intraoperative probe 20, 60, 80 into a patient's cavity. The surgeon is able to image the desired organ, tissue, vessel, or blood flow from a desired angle or location as a function of the pre-selected shape or rotation of the probe 20, 60, 80. During use within the cavity, the probe 20, 60, 80 maintains a pre-selected angle of rotation. If a different angle of rotation is desired, the surgeon withdraws the ultrasound probe 20, 60, 80 and readjusts or rotates the adjustable section 28.

In alternative embodiments, an adjustable or adaptable section 28 is provided on an endocavity ultrasound probe. For example, a vaginal or esophageal ultrasound probe is provided where two separate rigid sections, such as a transducer section 26 and a handle section 24 may be rotated relative to each other. The image plane is positioned for more optimal imaging of the uterus, heart or other organ prior to insertion within the cavity.

While the invention has been described above by reference to various embodiments, it will be understood that many changes and modifications can be made without departing from the scope of the invention. For example, different mechanisms for allowing rotation and maintaining the rotation may be provided. Both pitch, yaw and relative axle rotation may be provided. As yet another example, probes with various handle or transducer housing shapes and sizes may be adapted with an adjustable section. The link mounts for the transducer section 26 can be used on the handle section 24 and vice versa.

It is therefore intended that the foregoing detailed description be understood as an illustration of the presently preferred embodiments of the invention, and not as a definition of the invention. It is only the following claims, including all equivalents that are intended to define the scope of the invention.

What is claimed is:

1. In an intraoperative ultrasound probe for insertion into a patient, the intraoperative ultrasound probe having a handle section and a transducer section, the transducer section including a transducer, an improvement comprising:

an adaptable section between the handle section and the transducer section, the adaptable section operable to allow bending movement of and maintain the position of the handle section relative to the transducer section without steering wires, the adaptable section being memory-less.

2. The probe of claim 1 wherein the adaptable section is operable to rotate the transducer section relative to the handle section.

3. The probe of claim 1 wherein the adaptable section is operable to maintain a plurality of positions of the transducer section relative to the handle section.

4. The probe of claim 1 wherein the adaptable section comprises a memoryless bendable section.

5. The probe of claim 1 wherein the adaptable section comprises a metal shaft.

6. The probe of claim 5 wherein the metal shaft comprises aluminum wire.

7. The probe of claim 1 wherein the adaptable section comprises a ball joint.

8. The probe of claim 7 further comprising a tensioned wire connected with the transducer section and the handle section through the ball joint.

9. The probe of claim 1 wherein the adaptable section comprises a latch.

10. The probe of claim 9 wherein the latch comprises a notched portion connected with one of the handle and transducer sections and a pawl connected with a different one of the handle and transducer sections.

11. The probe of claim 1 wherein the adaptable section comprsies a material more malleable in response to external force than absent the external force.

12. The intraoperative probe of claim 1 wherein the adjustable section is operable such that the spatial orientation of the transducer section with respect to the handle section is maintained free of change during use in the cavity.

13. An intraoperative or endocavity ultrasound probe for insertion into a cavity or surgical incision of a patient, the probe comprising:
   a transducer housing;
   a handle housing; and
   an adjustable section joining the transducer housing to the handle housing, the adjustable section having a flexible covering and a device to maintain an adjusted bent position of the transducer housing to the handle housing without a device for adjusting the adjustable section during use within the patient.

14. The probe of claim 13 wherein the adjustable section is operable to rotate the transducer housing relative to the handle housing.

15. The probe of claim 13 wherein the adjustable section is operable to maintain a plurality of positions of the transducer housing relative to the handle housing without user control while in the cavity or surgical incision.

16. The probe of claim 13 wherein the adjustable section comprises a memoryless bendable section.

17. The probe of claim 13 wherein the device comprises a metal shaft.

18. The probe of claim 13 wherein the device comprises a ball joint and a tensioned wire connected with the transducer housing and the handle housing through the ball joint.

19. The probe of claim 13 wherein the adjustable section comprises latch having a notched portion connected with one of the handle and transducer housings and a pawl connected with a different one of the handle and transducer housings.

20. The probe of claim 13 wherein the flexible covering comprises a silicone based elastomer.

21. A method for using an intraoperative or endocavity ultrasound probe, the method comprising the acts of:
   (a) inserting the probe into a cavity of a patient;
   (b) rotating a first axis of a transducer housing relative to second axis of a handle housing prior to (a); and
   (c) maintaining a relative position of the first and second axes while the transducer housing is within the cavity.

22. The method of claim 21 wherein (c) comprises maintaining one or a plurality of possible relative positions.

23. The method of claim 21 wherein (b) comprises rotating in a pitch angle of the first axis to the second axis.

24. The method of claim 21 wherein (b) and (c) comprise bending a metal shaft.

25. The method of claim 21 wherein (b) and (c) comprises adjusting a ball joint having a tensioned wire connected with the transducer housing and the handle housing through the ball joint.

26. The method of claim 21 wherein (b) and (c) comprise adjusting a latch having a notched portion connected with one of the handle and transducer housings and a pawl connected with a different one of the handle and transducer housings.

27. The method of claim 21 further comprising:
   (d) increasing the malleability of the probe in response to an external force prior to (b).

* * * * *